(12) United States Patent
Thiebault et al.

(10) Patent No.: US 9,232,793 B2
(45) Date of Patent: *Jan. 12, 2016

(54) METHODS OF INHIBITING MICROBIAL GROWTH USING DEOXYALDOHEXOSES

(71) Applicants: LVMH Recherche, Saint Jean de Braye (FR); Universite de Picardie Jules Verne, Amiens (FR)

(72) Inventors: Nicolas Thiebault, Amiens (FR); Jean-Christophe Archambault, Meung sur Loire (FR); Patrice Andre, Neuville aux Bois (FR); Florence Pilard, Amiens (FR); Vincent Moreau, Amiens (FR)

(73) Assignee: LVMH Recherche, Amiens (FR)

( * ) Notice: Subject to any disclaimer, the term of this patent is extended or adjusted under 35 U.S.C. 154(b) by 118 days.

This patent is subject to a terminal disclaimer.

(21) Appl. No.: 13/741,464

(22) Filed: Jan. 15, 2013

(65) Prior Publication Data

US 2013/0142742 A1   Jun. 6, 2013

Related U.S. Application Data

(63) Continuation of application No. 12/415,136, filed on Mar. 31, 2009, now Pat. No. 8,377,892.

(30) Foreign Application Priority Data

Apr. 2, 2008   (FR) ..................................... 08 52192

(51) Int. Cl.
| | |
|---|---|
| A01N 43/16 | (2006.01) |
| A61K 8/60 | (2006.01) |
| A61K 31/7028 | (2006.01) |
| A61K 31/7032 | (2006.01) |
| A23L 1/03 | (2006.01) |
| A23L 1/236 | (2006.01) |
| A61K 9/00 | (2006.01) |
| A61K 9/10 | (2006.01) |
| A61K 47/26 | (2006.01) |
| A61Q 19/00 | (2006.01) |

(52) U.S. Cl.
CPC .............. *A01N 43/16* (2013.01); *A23L 1/2363* (2013.01); *A61K 8/604* (2013.01); *A61K 9/0014* (2013.01); *A61K 9/10* (2013.01); *A61K 31/7028* (2013.01); *A61K 31/7032* (2013.01); *A61K 47/26* (2013.01); *A61Q 19/00* (2013.01); *A61K 2800/524* (2013.01)

(58) Field of Classification Search
CPC ....... A61K 8/602; A61K 8/406; A61K 8/604; A61K 31/7028; A61K 31/7032; A01N 43/16
See application file for complete search history.

(56) References Cited

U.S. PATENT DOCUMENTS

| | | | |
|---|---|---|---|
| 7,666,847 B2 | 2/2010 | Houlmont et al. | |
| 2001/0029247 A1 | 10/2001 | Boures et al. | |
| 2006/0046969 A1 | 3/2006 | Maggio | |
| 2007/0134187 A1* | 6/2007 | Houlmont et al. | ......... 424/70.13 |
| 2009/0274760 A1 | 11/2009 | Thiebault et al. | |

FOREIGN PATENT DOCUMENTS

| | | |
|---|---|---|
| DE | 102005005199 | 8/2006 |
| FR | 2861729 | 5/2005 |
| WO | WO 2006/107386 | 10/2006 |
| WO | WO 2006107386 | 10/2006 |

OTHER PUBLICATIONS

Sabin et al., FEBS Letters, 2006, 580, p. 982-987.*
Martearena et al., Bioresource Technology, 2003, 90, p. 297-303.*
Hudson, CS, J. Am. Chem. Soc., 1925, 47(1), p. 268-280.*
FDA Guidance for Industry: Container Closure Systems for Packaging Human Drugs and Biologics, May 1999.*
Hudson, C.S., J. Am. Chem. Soc., 1925, 47(1), p. 265-268.*
Wald, G., Ann. N. Y. Acad. Sci., 1957, 69, p. 352-368.*
Ferench, T.J. Bacteriol., 1980, 144(1), p. 7-11.
Houlmont, J.P. et al., Cosmetic Use Formulations Containing pentyl rhamnoside and cetyl rhamnoside; International Journal of Cosmetic Science, vol. 23, No. 6, Dec. 2001, pp. 363-368.
Koeltzow et al., Jaocs, 1984, 61 (10), p. 1651-1655.
Search Report dated Dec. 10, 2008 from French Application No. 0852192 filed Apr. 2, 2008.
Takeo et al., "Synthesis of methyl α- and β-maltotriosides and aryl β-maltotriosides" Carbohydrate Research, 48, Jun. 1976, 197-208.

* cited by examiner

*Primary Examiner* — Jonathan S Lau
(74) *Attorney, Agent, or Firm* — Baker & Hostetler LLP

(57) ABSTRACT

The present invention relates to the use of an alkyl glycoside or of a mixture of at least two alkyl glycosides as agent intended for inhibiting microbial growth, in particular in a cosmetic, pharmaceutical or food composition.

30 Claims, 1 Drawing Sheet

METHODS OF INHIBITING MICROBIAL GROWTH USING DEOXYALDOHEXOSES

CROSS REFERENCE TO RELATED APPLICATIONS

This application is a continuation of U.S. application Ser. No. 12/415,136, filed Mar. 31, 2009, which claims the benefit of French Application No. 0852192, filed Apr. 2, 2008, the entireties of which are incorporated by reference herein.

The present invention relates to a novel use of alkyl glycosides and of mixtures of alkyl glycosides having antimicrobial properties, and to compositions, in particular cosmetic, pharmaceutical or food compositions, comprising said alkyl glycosides.

BACKGROUND

Alkyl glycosides and their applications are known, in particular from the documents US 2006/0046969 and WO 2006/107386.

Patent application US 2006/0046969 discloses an antibacterial composition comprising at least one alkyl glycoside, at least one saccharide and at least one therapeutic agent.

International patent application WO 2006/107386 discloses a composition for inhibiting and/or treating vaginal infections comprising a non-ionic surfactant which may be an alkyl glycoside of formula $(Z)_n$—O—R, in which Z is a saccharide, and R is a generally linear alkyl group comprising between 8 and 30 carbon atoms.

However, the applicant has sought to enhance the performance of compounds of this chemical family for antimicrobial applications.

DESCRIPTION OF THE INVENTION

Accordingly, one main aim of the present invention is to provide a novel agent intended for inhibiting microbial growth, in particular in cosmetic, pharmaceutical or food compositions.

One main aim of the present invention is also to provide a novel agent intended for inhibiting microbial growth, which can be used in a composition, in particular a cosmetic, pharmaceutical or food composition, the advantage of which is being able to envisage the substitution of other agents or mixtures of agents having this same function, and which are conventionally used in the formula of the compositions, in particular cosmetic, pharmaceutical or food compositions. The present invention offers in particular the possibility to avoid using in compositions that are intended in particular to be applied to the skin of the body or the face or to superficial body growths, any preservative of the family of parabens, which are reputed to be toxic, and to protect these compositions with products which are non-toxic such as the alkyl glycosides of the invention, and which have an equivalent efficacy to that of the said preservatives against microbial organisms.

The aim of the invention is finally also to solve the technical problem by a solution that is simple, inexpensive and that can be used on an industrial and cosmetic scale.

A first subject of the present invention relates to the novel use of an alkyl glycoside or of a mixture of at least two alkyl glycosides as agent intended for inhibiting microbial growth, in particular in a cosmetic, pharmaceutical or food composition, characterized in that the alkyl glycoside, or the alkyl glycosides of said mixture, have the general formula (S)—O—R, in which (S) is a sugar unit or an oligosaccharide formed of a sequence of 2 to 8 identical or different sugar units, said sugar unit being a pentose or hexose type reducing sugar, or a derivative of these sugars, and R is an alkyl group comprising from 1 to 24 carbon atoms.

According to a particularly preferred variant, the alkyl glycoside is chosen from the compounds of general formula (I) $(S_1)$—O—$R_1$, in which $(S_1)$ is a deoxyaldohexose, and $R_1$ is an alkyl group comprising from 1 to 24 carbon atoms;

or the mixture of at least two alkyl glycosides is chosen from:

the mixtures comprising at least one compound chosen from the compounds of general formula (I) as defined above;

the mixtures comprising at least one compound chosen from the compounds of general formula (II) $(S_2)$—O—$R_2$, $(S_2)$ being a sugar unit or an oligosaccharide formed of a sequence of 2 to 8 identical or different sugar units, and $(R_2)$ being an alkyl group comprising from 1 to 6 carbon atoms, and at least one compound chosen from the compounds of general formula (III) $(S_3)$—O—$R_3$, $(S_3)$ being a sugar unit or an oligosaccharide formed of a sequence of 2 to 8 identical or different sugar units, and $R_3$ being an alkyl group comprising from 8 to 24 carbon atoms.

The invention also relates to the novel use of the compounds and of the mixtures according to the invention, in particular in cosmetic, pharmaceutical or food compositions where they are present in an effective concentration, for inhibiting microbial growth.

It relates particularly to the alkyl glycosides whose glycoside group is a deoxyaldohexose. Deoxyaldohexoses are sugars composed of six carbon atoms (hexose), in which one or more of their hydroxyl groups is substituted by a hydrogen atom. Among the deoxyaldohexoses, there may be mentioned fucose, rhamnose, quinovose or pneumose.

It also relates in particular to mixtures of alkyl glycosides in which the alkyl chains have a different length, and offer a synergistic effect when the effect of these mixtures is compared to the results obtained for the compounds tested individually.

While it is known that alkyl glycosides exhibit activity against various bacteria, fungi or yeasts because of their amphiphilic character, the present invention shows that the activity spectrum varies according to their structure. Thus, the specific use of alkyl glycosides in which the glycoside group is a deoxyaldohexose makes it possible to demonstrate the remarkable antimicrobial, and therefore preservative, properties of these compounds. Moreover, the combination of alkyl glycosides of different structure within mixtures makes it possible to obtain a complementary or even synergistic activity against numerous pathogenic microbes of the bacterium, fungus or yeast type.

According to the invention, the group R and/or $R_1$ and/or $R_2$ and/or $R_3$ may be a saturated alkyl group, preferably a saturated linear alkyl group.

In particular, the group R and/or $R_1$ and/or $R_3$ is preferably an alkyl group comprising from 8 to 16 carbon atoms, and in a particularly preferred manner a dodecyl group; and the group R and/or $R_2$ is in a particularly preferred manner a methyl group.

According to the invention, the deoxyaldohexose group $(S_1)$ may be chosen equally well from the laevorotatory sugar series (L-series) or dextrorotatory sugar series (D-series), but is chosen more particularly from the laevorotatory sugars.

The conditions for the synthesis of the alkyl glycosides according to the invention make it possible to specifically obtain compounds in which the bond between the sugar unit or the oligosaccharide (S) and the R group is either of the alpha type or of the beta type, or make it possible to arrive at a mixture of the same compound of which a fraction has this alpha type bond, and the resulting fraction has the same beta type bond.

According to the invention, the bond between the oligosaccharide (S) and the group R may be equally well of the alpha or beta type, and preferably of the beta type.

In particular, the bond between the deoxyaldohexose ($S_1$) and the alkyl group $R_1$ may be equally well of the alpha or beta type, and preferably of the beta type.

The deoxyaldohexose group is preferably chosen from fucose or rhamnose.

According to a preferred embodiment, the deoxyaldohexose group is chosen from beta-L-fucose and beta-L-rhamnose.

The alkyl glycosides used in the present invention are thus more particularly chosen from dodecyl L-fucoside and dodecyl L-rhamnoside.

According to the invention, in a first aspect, the group (S) and/or ($S_2$) and/or ($S_3$) may be a simple sugar unit, or an oligosaccharide formed of a sequence of 2 sugar units (disaccharide) or of 3 sugar units (trisaccharide).

According to the invention, the sugar unit(s) is (are) chosen more particularly from the dextrorotatory sugar series (D-series).

According to a preferred embodiment, the sugar unit(s) is (are) pentose or hexose type reducing sugars, or a derivative of these sugars, preferably a uronic derivative, a sulphate derivative or a deoxy derivative.

According to another preferred embodiment, the sugar unit(s) is (are) chosen from arabinose, xylose, ribose, glucose, galactose, mannose, rhamnose, fucose.

According to another particularly preferred embodiment, the sugar unit chosen is D-glucose.

According to the invention, in a second aspect, the group (S) and/or ($S_2$) and/or ($S_3$) is an oligosaccharide formed of a sequence of 2 to 8 sugar units.

The sequence of sugar units forming the oligosaccharide may be formed of the repeat of the same sugar unit or may be formed of different sugar units.

The sequence of sugar units forming the oligosaccharide may be linear or branched.

The linkages between the sugar units are formed by a covalent glycosidic bond between the reducing group (hydroxyl) of the alcohol functional group of the hemiacetal carbon of a sugar (anomeric carbon, number 1) and the acid group (free hydrogen) of another molecule.

This bond may be equally well of the alpha or beta type, and preferably of the beta type.

The glycosidic bond may be of the 1-3 type, that is to say between the anomeric carbon No. 1 of the first sugar, and the hydroxyl group of carbon No. 3 of the second sugar, of the 1-4 type, or of the 1-6 type.

The bond is preferably of the 1-4 type.

According to a preferred embodiment, the oligosaccharide may be chosen from maltose, cellobiose, lactose, fructose, maltotriose, cellotriose.

The oligosaccharide may be laevorotatory (L-) or dextrorotatory (D-), and is preferably chosen from the oligosaccharides of the (D-) series.

According to another preferred embodiment, the oligosaccharide is chosen from beta-D-maltose or beta-D-maltotriose.

According to the invention, at least one of the alkyl glycosides used may be chosen from dodecyl beta-L-rhamnoside, dodecyl beta-L-fucoside, methyl beta-D-maltoside, methyl beta-D-maltotrioside, dodecyl beta-D-maltoside, dodecyl beta-D-maltotrioside.

In a first preferred variant, a mixture is used which is composed of two alkyl glycosides which are present in the mixture in a ratio of between 1/99 and 99/1, preferably of between 75/25 and 25/75, preferably still of about 50/50.

A first preferred mixture is formed by methyl beta-D-maltoside and an alkyl glycoside formed of a sequence of 3 sugar units, preferably dodecyl beta-D-maltotrioside.

Another preferred mixture is formed by methyl beta-D-maltotrioside and an alkyl glycoside formed of a sequence of 2 sugar units, preferably dodecyl beta-D-maltoside.

In particular, a preferred mixture is formed by the set of two alkyl glycosides characterized in that it comprises dodecyl beta-D-maltotrioside.

According to this embodiment, a particularly preferred mixture is that formed by dodecyl beta-D-maltotrioside and methyl beta-D-maltoside.

In a second preferred variant, a mixture of alkyl glycosides is used which is composed of four alkyl glycosides.

Preferably, the four alkyl glycosides are present in the mixture in substantially equal proportions.

In particular, a preferred mixture is formed by methyl beta-D-maltoside, methyl beta-D-maltotrioside, dodecyl beta-D-maltoside, dodecyl beta-D-maltotrioside.

In general, in the case of mixtures according to the invention, it is preferable in particular to combine alkyl glycosides which have different sugar or deoxysugar groups and/or alkyl groups of substantially different lengths.

This thus makes it possible to cover a broader spectrum because of the different sensitivity of the microbes according to the structure of the compounds.

Finally, the alkyl glycosides or mixtures of alkyl glycosides according to the invention are used in a sufficient quantity to provide an antimicrobial effect such that it allows the preservation and bacteriological stability of the composition, in particular the cosmetic, pharmaceutical or food composition.

According to the invention, the microbial growth inhibiting agent is preferably present in an amount of 0.001% to 10% by weight of the composition containing it, in particular of 0.01% to 5% by weight of the said composition.

Such mixtures according to the invention thus allow the preparation of a cosmetic or pharmaceutical composition free of any other preservative.

A second subject of the present invention relates to a cosmetic, pharmaceutical or food composition, characterized in that it comprises, in particular as agent intended for inhibiting microbial growth, a mixture of at least two alkyl glycosides chosen from:

the mixtures comprising at least one compound chosen from the compounds of general formula (I) ($S_1$)—O—$R_1$, in which ($S_1$) is a deoxyaldohexose, and $R_1$ is an alkyl group comprising from 1 to 24 carbon atoms;

the mixtures comprising at least one compound chosen from the compounds of general formula (II) ($S_2$)—O—$R_2$, ($S_2$) being a sugar unit or an oligosaccharide formed of a sequence of 2 to 8 identical or different sugar units, and ($R_2$) being an alkyl group comprising from 1 to 6 carbon atoms, and at least one compound chosen from the compounds of general formula (III) ($S_3$)—O—$R_3$, ($S_3$) being a sugar unit or an oligosaccharide formed of a sequence of 2 to 8 identical or different sugar units, and $R_3$ being an alkyl group comprising from 8 to 24 carbon atoms.

According to the invention, said mixture is in particular as defined in the preceding considerations relating to the first subject of the invention.

According to the invention, the composition further preferably comprises at least one cosmetically or pharmaceutically active agent and at least one cosmetically or pharmaceutically acceptable excipient.

The cosmetic composition may equally well be a care product for the skin or the superficial body growths, a makeup product or a health-care product, such as a shampoo, a cleansing or makeup-removing product for the skin or the superficial body growths.

According to a preferred embodiment, the composition is intended for application to all or part of the skin of the face or of the body, or to the superficial body growths.

In particular, said composition may be a serum, a lotion, an emulsion, preferably a care cream, a hydrogel, preferably a mask, a mascara, a foundation, an eyeshadow, an eyeliner, or may be provided in the form of a stick.

The cosmetically active agent may be for example a compound chosen from substances having a skin lightening activity; a substance from those having a slimming activity; substances having a moisturizing activity; substances having a calming, soothing or relaxing activity; substances having a skin microcirculation stimulating activity in order to enhance the radiance of the complexion; substances having a sebo-regulating activity for greasy skin care; substances intended to cleanse or purify the skin; substances having an anti-free radical activity; substances intended to attenuate or delay the effects of skin ageing.

The cosmetically acceptable excipient may be chosen from the group comprising pigments, colorants, polymers, surfactants, rheology-promoting agents, perfumes, electrolytes, pH-adjusting agents, antioxidants, preservatives, and mixtures thereof.

According to the invention, the composition preferably comprises from 0.001% to 10% by weight of the abovementioned mixture, in particular from 0.01% to 5% by weight of the abovementioned mixture.

The alkyl glycosides or mixtures of at least two alkyl glycosides as defined according to the invention are used in an effective quantity, in particular in cosmetic, pharmaceutical or food compositions, to ensure the microbiological stability of the composition by avoiding the growth of microbes of the bacterium, fungus or yeast type.

Accordingly, a composition comprising such a mixture of alkyl glycosides according to the invention may be completely free of any other agent intended to inhibit microbial growth, in particular of compounds of the paraben family.

Other aims, characteristics and advantages of the invention will emerge clearly in the light of the explanatory description which follows, which is made with reference to various exemplary embodiments of the invention given solely by way of illustration and which cannot therefore in any way limit the scope of the invention. In the examples, all the percentages are given by weight, the temperature is in degrees Celsius, the pressure is atmospheric pressure, unless otherwise stated.

Figure 1:
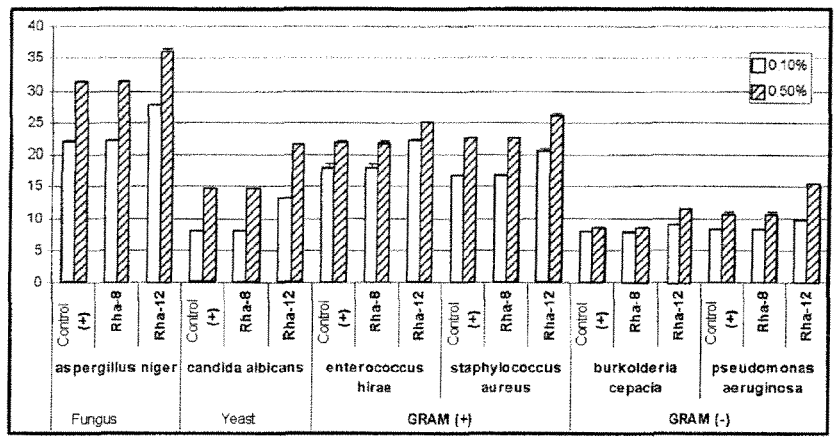
FIG. 1 is given with reference to Example 3a), and presents the germicidal activity of alkylated derivatives of rhamnose.

It will be noted that for each of these figures, the inhibition diameter, which is measured in millimeters, is represented on the y-axis.

Materials and Methods

1. Synthesis of the Compounds

Unless otherwise stated, the various alkyl glycosides are synthesized according to the method described by Takeo et al. (*Carbohydrate Research*, 48 (1976) 197-208).

The method of synthesis used here differs from the publication only in the glycosylation step (grafting of the alkyl chain), in which benzene is substituted by dichloromethane ($CH_2Cl_2$) and mercury acetate is replaced by a mixture HgO/$HgBR_2$. This step is specifically described for each of the compounds exemplified below.

The choice of the compounds of the reaction, of the catalysts and of the reaction conditions so as to carry out the reaction to completion with a sufficient yield is well known in the state of the art.

The products synthesized in order to then be tested are the following:

Rha-1: methyl L-rhamnoside, prepared according to Example 1.
Rha-8: octyl L-rhamnoside
Rha-12: dodecyl L-rhamnoside
Fuc-8: octyl beta-L-fucoside, prepared according to Example 2.
Fuc-12: dodecyl beta-L-fucoside
DP2-1: methyl beta-D-maltoside, prepared according to Example 4.
DP2-12: dodecyl beta-D-maltoside, origin ACROS ORGANICS.
DP3-1: methyl beta-D-maltrioside, prepared according to Example 5.
DP3-12: dodecyl beta-D-maltotrioside, prepared according to Example 6.

2. Test for Measuring the Antimicrobial Activity of Alkyl Glycosides and of Mixtures of Alkyl Glycosides a) Principle of the Test The culture medium at pH 6, pH 7 and pH 8, inoculated beforehand with the test strains, is poured into Petri dishes, with one pH and one strain per dish.

After solidification, 100 µl are deposited for each of the concentrations of the test substance, as well as a solvent control and a positive control.

After incubation, the inhibition diameter is measured after diffusion of the test product into the agar, and there is deduced therefrom the minimum bacteriostatic concentration (MIC), which is the lowest concentration of product inhibiting the multiplication of the microbes.

b) Materials and Methods

Materials
Sterile Petri dishes Ø 90 mm with ergots,
Vernier caliper,
Sterile steel cylinders.

Culture Media
Agar medium B: agar medium with soybean and casein peptones,
Agar medium C: Sabouraud-glucose-agar medium with chloroamphenicol,
Tryptone salt,
Diluent for moulds,
Buffer NaCl,
Mueller-Hinton medium pH 7.

Reagents
Sterile water,
Methanol,
KATHON® (origin Röhm & Haas).

Strains

The test strains are the following:
*Aspergillus niger* IP 1431.83,
*Candida albicans* IP 48.72,
*Enterococcus hirae* CIP 58.55,
*Staphylococcus aureus* CIP 4.83,
*Burkholdena cepacia* CIP 103924,
*Pseudomonas aeruginosa* CIP 82.1118.

c) Inoculation of the Culture Media

For each strain, 120 ml of each of the three Mueller Hinton media pH 6, pH 7 and pH 8 are inoculated with 1.2 ml of each suspension of microbe having a titre of $10^7$ CFU/ml in order to obtain a titre equal to $10^5$ CFU/ml.

15 ml are poured into each dish, with one dish per medium and per strain. After solidification, three steel cylinders are placed at the surface of each dish.

Preparation of the Test Product Concentration Range 100 mg (approximately) of the powder consisting of the test alkyl glycoside are taken up in 1 ml of methanol (solution A at 10%).

Next, the concentration range is prepared as described below:
Solution B1 at 1%: 300 μl of solution A+2.7 ml of sterile water,
Solution B2 at 0.5%: 300 μl of solution A+5.7 ml of sterile water,
Solution B3 at 0.1%: 1 ml of solution B1+9 ml of sterile water,
Solution B4 at 0.05%: 1 ml of solution B2+9 ml of sterile water.

Only solutions B2, B3 and B4 are tested during the trial.

Preparation of a Solvent Control

A 1/10 dilution of methanol in sterile water is prepared.

Deposition of the Test Solution and Incubation

100 μl (pH 6, pH 7 and pH 8) of the following solutions are introduced into each cylinder:
Methanol control (prepared for each strain at pH 7),
Solution B4 at 0.05%,
Solution B3 at 0.1%,
Solution B2 at 0.5%.

Incubation at 37° C.±1° C. for 24 hours (48 h for *Enterococcus hirae*).

Determination of the Minimum Inhibitory Concentration (MIC)

The inhibition of growth of the microbes leads to measurement, using a vernier caliper, in millimeters, of an inhibition diameter after diffusion of the test product into the agar.

The minimum bacteriostatic concentration (MIC) is given by the lowest concentration of product which inhibits the multiplication of the microbes.

In the case where the highest concentration (500 μm/ml) is not active, this is noted (>500).

EXAMPLES

Example 1

Synthesis of Dodecyl L-rhamnoside

A solution of 3 grams of L-rhamnose in 100 ml of pyridine is prepared.

The intermediate step specific to the method consists in adding 37 ml of dodecanol to 2,3,4-tri-O-acetyl-rhamnopyranosyl bromide (5.817 g) obtained at the end of the initial steps of the method, in solution in dichloromethane (120 ml), and $CaSO_4$ ground into a fine powder (11.21 g), HgO yellow powder (5.647 g) and $HgBr_2$ (280 mg).

The method of synthesis according to Takeo et al. is carried out to its completion and leads to dodecyl L-rhamnoside.

The overall yield of synthesis is 54.9%.

Example 2

Synthesis of Octyl L-fucoside

A solution of 1.77 grams of L-fucose in 70 ml of pyridine is prepared to which 35 ml of acetic anhydride are added.

The step specific to the method of synthesis consists in adding 17 ml of octanol to 2,3,4-tri-O-acetyl-fucopyranosyl bromide (3.81 g) obtained at the end of the initial steps of the method, in solution in dichloromethane (75 ml), and $CaSO_4$ ground into a fine powder (7.34 g), HgO yellow powder (3.69 g) and $HgBr_2$ (183 mg).

The method of synthesis according to Takeo et al. is carried out to its completion and leads to octyl L-fucoside.

The overall yield of synthesis is 58.6%.

Example 3

Microbe Growth Inhibition Activity

The tests were carried out on various strains at pH 7, for alkyl glycoside concentrations equal to 0.05%, 0.1% and 0.5% by weight.

a) Microbe Growth Inhibition Activity in the Presence of Alkylated Derivatives of Rhamnoside The activity on various microbes of each of the compounds Fuc-1, Fuc-8 and Fuc-12 is evaluated, compared with that of a positive control, KATHON®, used in the same concentration range.

Three concentrations (0.05%, 0.1% and 0.5%) are tested in order to evaluate the effect of the concentration on the growth of the microbes.

The results are represented in the accompanying FIG. 1 for the two highest concentrations.

The MIC for each of the strains is determined for each molecule tested (Table 1 below):

TABLE 1

Determination of the MIC values for alkyl rhamnosides at pH 7 in μg/ml and in (μM).

|  | Rha-8 | Rha-12 |
|---|---|---|
| P. aeruginosa | 100 (362) | 50 (150) |
| B. cepacia | 100 (362) | 100 (301) |
| E. hirae | 50 (181) | 50 (150) |
| S. aureus | 50 (181) | 50 (150) |
| C. albicans | 100 (362) | 50 (150) |
| A. niger | 50 (181) | 50 (150) |

Conclusions

The two compounds exhibit an inhibitory activity towards all the strains tested.

b) Microbe Growth Inhibition Activity in the Presence of Alkylated Derivatives of Fucose The activity on various microbes of each of the compounds Fuc-1, Fuc-8 and Fuc-12 is evaluated, and compared with that of a positive control, KATHON®, used in the same concentration range.

Three concentrations are tested in order to evaluate the effect of the concentration on the growth of the microbes.

Figure 2:
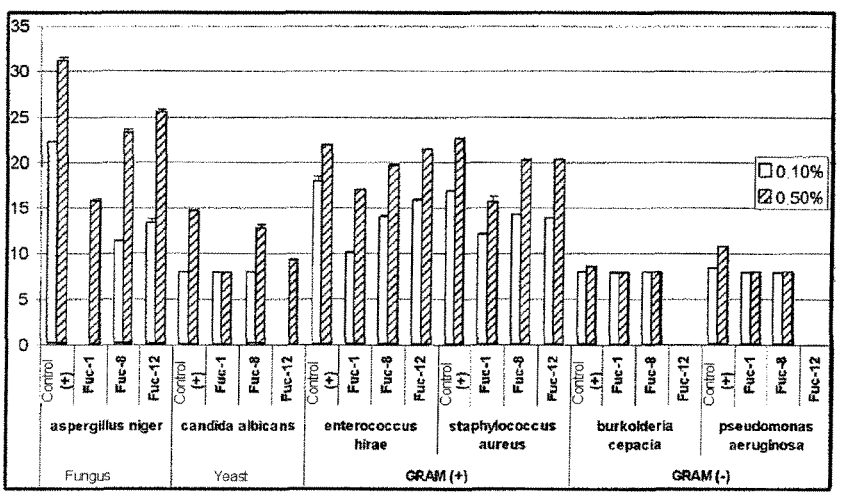
FIG. 2 is given with reference to Example 3b), and presents the germicidal activity of alkylated derivatives of fucose.

The results are presented in the accompanying FIG. 2.

The MIC for each of the strains is determined for each molecule tested (Table 2 below):

TABLE 2

Summary of the antimicrobial tests on the alkyl fucosides at pH 7 in µg/ml and in (µM).

|  | Fuc-1 | Fuc-8 | Fuc-12 |
|---|---|---|---|
| P. aeruginosa | >500 (>2800) | >500 (>1810) | >500 (>1500) |
| B. cepacia | >500 (>2800) | >500 (>1810) | >500 (>1500) |
| E. hirae | 50 (280) | 50 (181) | 50 (150) |
| S. aureus | 50 (280) | 50 (181) | 50 (150) |
| C. albicans | >500 (>2800) | 100 (362) | >500 (>1500) |
| A. niger | 100 (562) | 50 (181) | 50 (150) |

Conclusions

The alkylated derivatives of fucose appear to exhibit a lower activity towards the microbes than the rhamnose derivatives of the preceding example.

Moreover, these compounds exhibit no activity towards Gram(−) bacteria.

On the other hand, these molecules exhibit activity towards Gram(+) bacteria, regardless of the length of the alkyl chain grafted to the fucose.

Example 4

Synthesis of Methyl Maltoside

A solution of 5 grams of D-maltose in 220 ml of pyridine is prepared and 80 ml of acetic anhydride (80 ml) are added.

The intermediate step specific to the method consists in adding 5.5 ml of methanol to a solution of 2,2',3,3',4',6,6'-hepta-O-acetyl-alpha-D-maltosyl bromide (2.05 g) in dichloromethane (16.5 ml), and there are added 5.5 ml of methanol, $CaSO_4$ ground to a fine powder (2 g), HgO yellow powder (1 g) and $HgBr_2$ (49 mg).

The method of synthesis leads to methyl beta-D-maltoside.

The overall yield of synthesis is 75.4%.

Example 5

Synthesis of Methyl Maltotrioside

A solution of 5 grams of D-maltotriose in 150 ml of pyridine (150 ml) is prepared and 50 ml of acetic anhydride are added.

The intermediate step specific to the method consists in adding 6 ml of methanol to 2,2',2'',3,3',3'',4',4'',6,6',6''-deca-O-acetyl-alpha-D-maltotriosyl bromide (2.878 g) obtained at the end of the first steps of the method, in solution in dichloromethane (20 ml), and $CaSO_4$ ground to a fine powder (2 g), HgO yellow powder (1 g) and $HgBr_2$ (49 mg).

The method of synthesis according to Takeo et al. is carried out to its completion and finally leads to methyl beta-D-maltotrioside.

The overall yield of the method of synthesis is 85%.

Example 6

Synthesis of Dodecyl Maltotrioside

A solution of 1.5 grams of D-maltotriose (2.97 mmol) in 50 ml of pyridine is prepared to which 15 ml of acetic anhydride are added.

The step specific to the method of synthesis consists in adding 6.75 ml of dodecanol to 2,2',2'',3,3',3'',4',4'',6,6',6''-deca-O-acetyl-alpha-D-maltotriosyl bromide (2.93 g) obtained at the end of the initial steps of the method, in solution in 20 ml of dichloromethane, and $CaSO_4$ ground to a fine powder (2.02 g), HgO yellow powder (1.017 g) and $HgBr_2$ (50.6 mg).

The method of synthesis according to Takeo et al. is carried out to its completion and finally leads to dodecyl beta-D-maltotrioside.

The overall yield of synthesis is 77.1%.

Example 7

Microbe Growth Inhibition Activity, in the Presence of Binary Mixtures of Alkyl Glycosides Comprising a Methyl Oligosaccharide (DPx-1) and a Dodecyl Oligosaccharide (DPy-12) with x=2 or 3, y=2 or 3, and x=y or x≠y The activity of the mixtures of alkyl glycosides A, B, C, D described below is evaluated on various microbes:

A=DP2-1+DP2-12 (1:1)
B=DP3-1+DP3-12 (1:1)
C=DP2-1+DP3-12 (1:1)
D=DP2-12+DP3-1 (1:1)

Two concentrations of mixtures are tested in order to evaluate the effect of these mixtures on the growth of the microbes.

Figure 3:
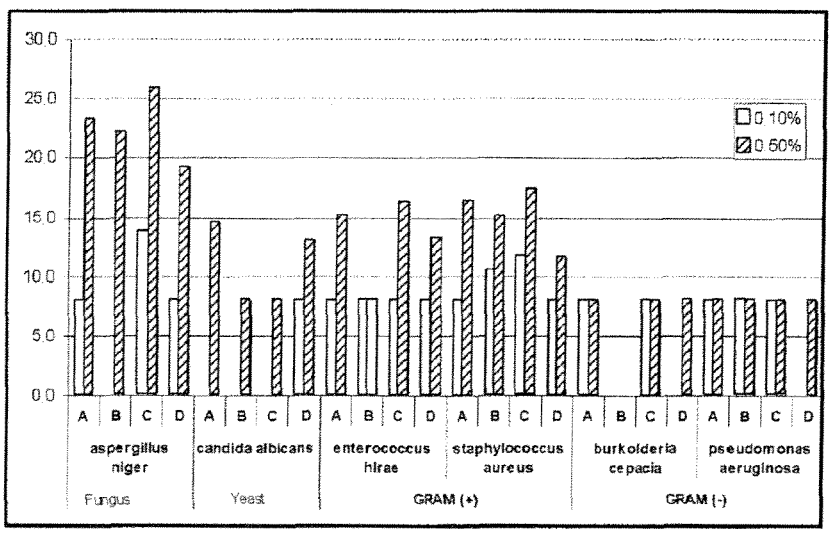
FIG. 3 is given with reference to Example 7, and presents the germicidal activity of mixtures of alkyl glycosides.

The results are represented in the accompanying FIG. 3.

Conclusions

The mixtures tested exhibit no significant activity on GRAM(−) bacteria.

However, their activity starting from a concentration equal to 0.5% on other microbes confers complementary properties on them as preservative, making their use in cosmetic compositions particularly advantageous.

This activity allows an adjustment of the composition of preservative in the cosmetic compositions of the invention.

Example 8

Anti-Ageing Emulsion Cream Containing Dodecyl L-rhamnoside According to the Invention The percentages are expressed by weight relative to the final composition:

| | |
|---|---|
| Plant extract of Centella asiatica | 0.1 |
| Surfactant (Arlacel ® 165 VP) | 5 |
| Cetyl alcohol 95% | 1 |
| Stearyl alcohol | 1 |
| Beeswax | 1.5 |
| Oil (Perleam ®) | 8.5 |
| Tricaprate/caprylate glycerides | 3 |
| Silicone oil (dimethicone 100 CS) | 1 |
| Polymer (Keltrol ®) | 0.35 |
| Sodium hydroxide | 0.04 |
| EDTA tetrasodium powder | 0.1 |
| Dodecyl L-rhamnoside | 0.5 |
| Water | qs 100 |

Example 9

Foundation Containing a Mixture of Two Alkyl Glycosides According to the Invention, as Microbial Growth Inhibiting Agent The percentages are expressed by weight relative to the final composition:

| | |
|---|---|
| Mica | 31 |
| Titanium dioxide | 22.4 |
| Talc | 11 |
| Anhydrous silica | 6 |
| Nylon-12 | 8 |
| Octyl methoxycinnamate | 7 |
| Methyl phenyl polysiloxane | 2.5 |
| Stearic acid | 2 |
| Magnesium stearate | 1.5 |
| Colorants (iron oxides) | 2.5 |
| Phenyl trimethicone | 2 |
| Glycerine | 2 |
| Methyl beta-D-maltoside | 0.5 |
| Dodecyl beta-D-maltotrioside | 0.5 |
| Perfume, colorants, neutralizing agent | qs |

Example 10

Shampoo Containing a Mixture of Four Alkyl Glycosides According to the Invention, as Microbial Growth Inhibiting Agent The percentages are expressed by weight relative to the final composition:

| | |
|---|---|
| Crosslinked sodium polyacrylate | 4 |
| Sodium laureth sulphate | 11.9 |
| Cocamidopropylbetaine | 2.5 |
| PEG-9 cocoglycerides | 2.5 |
| Sodium cocoyl hydrolysed wheat protein | 0.9 |
| Methyl beta-D maltoside | 0.25 |
| Methyl beta-D-maltotrioside | 0.25 |
| Dodecyl beta-D-maltoside | 0.25 |
| Dodecyl beta-D-maltotrioside | 0.25 |
| Pigment, perfumes, antioxidants | qs |
| Purified water | qs 100 |

It will be noted that the compositions according to the invention described above in Examples 8 to 10 are protected against microbial contamination with one or more alkyl glycosides, and consequently contain no other agent aimed at inhibiting microbial growth, in particular no preservative of the paraben family.

The invention claimed is:

1. A method for inhibiting the growth of Gram(+) bacteria in a composition comprising:
   identifying a composition in need of Gram(+) bacteria growth inhibition; and
   incorporating in the composition, an antimicrobial agent comprising:
   an alkyl glycoside or a mixture of at least two alkyl glycosides, wherein the alkyl glycoside, or at least one of the alkyl glycosides of said mixture, is of formula (I)

$(S_1)$—O—$R_1$  (I)

wherein $(S_1)$ is a deoxyaldohexose and $R_1$ is an alkyl group comprising from 1 to 24 carbon atoms; and wherein the deoxyaldohexose is a fucose, rhamnose, quinovose, pneumose, or a mixture thereof;
   wherein the antimicrobial agent is present in an amount of from 0.01% to 5%, by weight of the composition, which is sufficient to inhibit the growth of Gram(+) bacteria.

2. The method according to claim 1, wherein the deoxyaldohexose is a laevorotatory sugar.

3. The method according to claim 1, wherein the deoxyaldohexose is beta-L-fucose, beta-L-rhamnose, or a mixture thereof.

4. The method according to claim 1, wherein at least one of said alkyl glycosides is of the formula (S)—O—R wherein (S) is an oligosaccharide formed of a sequence of 2 to 8 identical or different sugar units, said sugar unit being a pentose- or hexose-containing reducing sugar; and R is an alkyl group comprising from 1 to 24 carbon atoms.

5. The method according to claim 1, wherein at least one of said alkyl glycoside is of formula (II)

$(S_2)$—O—$R_2$  (II)

wherein $(S_2)$ is an oligosaccharide formed of a sequence of 2 to 8 identical or different sugar units; and $R_2$ is an alkyl group comprising from 1 to 6 carbon atoms.

6. The method according to claim 1, wherein at least one of said alkyl glycoside is of formula (III)

$(S_3)$—O—$R_3$  (III)

wherein $(S_3)$ is an oligosaccharide formed of a sequence of 2 to 8 identical or different sugar units; and $R_3$ is an alkyl group comprising from 8 to 24 carbon atoms.

7. The method according to claim 1, wherein said composition is a cosmetic composition.

8. The method according to claim 1, wherein said composition is a pharmaceutical composition.

9. The method according to claim 1, wherein said composition is a food composition.

10. The method according to claim 1, wherein $R_1$ is an alkyl group having from 8 to 16 carbon atoms.

11. The method according to claim 1, wherein $R_1$ is a dodecyl group.

12. The method according to claim 1, wherein $R_1$ is a methyl group.

13. The method according to claim 1, wherein $R_1$ is an octyl group.

14. The method according to claim 1, wherein at least one of the alkyl glycosides is methyl L-rhamnoside, octyl L-rhamnoside, dodecyl L-rhamnoside, octyl beta-L-fucoside, dodecyl beta-L-fucoside, or a mixture thereof.

15. The method according to claim 1, wherein at least one of the alkyl glycoside is methyl L-rhamnoside.

16. The method according to claim 1, wherein at least one of the alkyl glycoside is octyl L-rhamnoside.

17. The method according to claim 1, wherein at least one of the alkyl glycoside is dodecyl L-rhamnoside.

18. The method according to claim 1, wherein at least one of the alkyl glycoside is octyl beta-L-fucoside.

19. The method according to claim 1, wherein at least one of the alkyl glycoside is dodecyl beta-L-fucoside.

20. The method according to claim 1, further comprising at least one alkyl glycoside that is methyl beta-D-maltoside, methyl beta-D-maltotrioside, dodecyl beta-D-maltoside, or dodecyl beta-D-maltotrioside.

21. The method according to claim 1, wherein the alkyl glycoside or the mixture of at least two alkyl glycosides is present in an amount of about 0.5%, by weight of the composition.

22. The method according to claim 1, wherein the mixture comprises two alkyl glycosides in a relative weight ratio of between 1/99 and 99/1.

23. The method according to claim 1, wherein the alkyl glycoside or the mixture of at least two alkyl glycosides is present in an amount of about 1%, by weight of the composition.

24. A method of cosmetic care for inhibiting Gram(+) bacterial growth comprising:
applying, to at least one body zone in need of Gram(+) bacterial growth inhibition, a composition comprising an antimicrobial agent comprising an alkyl glycoside or a mixture of at least two alkyl glycosides, wherein the alkyl glycoside, or at least one of the alkyl glycosides of said mixture, is of formula (I)

$$(S_1)\text{—O—}R_1 \quad (I)$$

wherein $(S_1)$ is a deoxyaldohexose; and $R_1$ is an alkyl group comprising from 1 to 24 carbon atoms; and wherein the deoxyaldohexose is a fucose, rhamnose, quinovose, pneumose, or a mixture thereof;
wherein the antimicrobial agent is present in an amount of from 0.01% to 5%, by weight of the composition, which is sufficient to inhibit the growth of Gram(+) bacteria on the body zone.

25. The method of cosmetic care according to claim 24, wherein the composition further comprises at least one cosmetically acceptable excipient.

26. The method of cosmetic care according to claim 24, wherein the compositions further comprises at least one cosmetically acceptable excipient selected from the group consisting of pigments, colorants, polymers, surfactants, rheology-promoting agents, perfumes, electrolytes, pH-adjusting agents, antioxidants, preservatives, and mixtures thereof.

27. The method of cosmetic care according to claim 24, wherein said composition is formulated in a cosmetic form selected from the group consisting of a serum, a lotion, an emulsion, a care cream, a hydrogel, a mask, a mascara, a foundation, an eyeshadow, an eyeliner, and a stick.

28. The method of cosmetic care according to claim 24, wherein said composition comprises about 0.5%, by weight of the composition, of said alkyl glycoside or of said mixture of alkyl glycosides.

29. The method of cosmetic care according to claim 24, wherein said composition comprises, as sole agent intended for inhibiting microbial growth, said alkyl glycoside or said mixture of alkyl glycosides.

30. The method of cosmetic care according to claim 24, wherein said composition comprises about 1%, by weight of the composition, of said alkyl glycoside or of said mixture of alkyl glycosides.

* * * * *